(12) United States Patent
Amthor et al.

(10) Patent No.: US 12,205,711 B2
(45) Date of Patent: Jan. 21, 2025

(54) CROSS-VENDOR CROSS-MODALITY IMAGING WORKFLOW ANALYSIS

(71) Applicant: KONINKLIJKE PHILIPS N.V., Eindhoven (NL)

(72) Inventors: Thomas Erik Amthor, Hamburg (DE); Jörn Borgert, Hamburg (DE); Joachim Schmidt, Hamburg (DE); Eberhard Sebastian Hansis, Munich (DE); Thomas Netsch, Hamburg (DE); Michael Günter Helle, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 905 days.

(21) Appl. No.: 17/261,771

(22) PCT Filed: Jul. 17, 2019

(86) PCT No.: PCT/EP2019/069302
§ 371 (c)(1),
(2) Date: Jan. 20, 2021

(87) PCT Pub. No.: WO2020/020731
PCT Pub. Date: Jan. 30, 2020

(65) Prior Publication Data
US 2021/0350911 A1    Nov. 11, 2021

Related U.S. Application Data

(60) Provisional application No. 62/702,462, filed on Jul. 24, 2018.

(51) Int. Cl.
*G16H 40/20* (2018.01)
*G01R 33/56* (2006.01)
(Continued)

(52) U.S. Cl.
CPC ......... *G16H 40/20* (2018.01); *G01R 33/5608* (2013.01); *G01T 1/161* (2013.01);
(Continued)

(58) Field of Classification Search
CPC ........ G16H 40/20; G16H 40/67; G16H 10/60; G16H 30/20; G16H 50/70; G16H 70/20;
(Continued)

(56) References Cited

U.S. PATENT DOCUMENTS

| 2004/0054248 | A1* | 3/2004 | Kimchy | A61B 5/06 600/3 |
| 2007/0118399 | A1* | 5/2007 | Avinash | G16H 40/20 705/2 |

(Continued)

FOREIGN PATENT DOCUMENTS

| GB | 2497079 A | * | 6/2013 | ......... A61B 5/02055 |
| WO | 2017102860 A1 | | 6/2017 | |
| WO | 2017129564 A1 | | 8/2017 | |

OTHER PUBLICATIONS

"A, Hosny, 'Artificial Intelligence in Radiology', Aug. 2018, HHS Public Access, edition 18(8) available in Nov. 2018, pp. 1-27" (Year: 2018).*

(Continued)

*Primary Examiner* — Chan S Park
*Assistant Examiner* — D J Dhooge (57) ABSTRACT

When acquiring detailed utilization information from imaging equipment in a cross-vendor approach, one or more sensors (16, 18, 22, 24) are positioned within a data security zone (14) in which an imaging procedure is performed. Sensor data is pre-processed on an isolated processing unit (20) to remove any sensitive information and keep a selection of features only. The resultant feature pattern is transmitted outside of the data security zone to a processing unit (Continued)

(28) where pattern recognition is performed on feature pattern to identify the type of imaging modality, scan, etc. being performed as well as to determine whether the scan is being performed according to schedule.

20 Claims, 3 Drawing Sheets (51) Int. Cl.
G01T 1/161 (2006.01)
G06N 20/00 (2019.01)
G10L 25/78 (2013.01)
G16H 10/60 (2018.01)
G16H 30/20 (2018.01)
G16H 40/67 (2018.01)
G16H 50/70 (2018.01)
G16H 70/20 (2018.01)

(52) U.S. Cl.
CPC ............. *G06N 20/00* (2019.01); *G16H 10/60* (2018.01); *G16H 30/20* (2018.01); *G16H 40/67* (2018.01); *G16H 50/70* (2018.01); *G16H 70/20* (2018.01); *G06F 2218/08* (2023.01); *G06F 2218/12* (2023.01); *G10L 25/78* (2013.01)

(58) Field of Classification Search
CPC .... G06N 20/00; G01R 33/5608; G01T 1/161; G06F 2218/12; G06F 2218/08; G10L 25/78
See application file for complete search history.

(56) References Cited

U.S. PATENT DOCUMENTS

| 2011/0121969 | A1 | 5/2011 | Mercer et al. |
| 2011/0245632 | A1* | 10/2011 | Chutani ................ G16H 40/67 600/301 |
| 2013/0049966 | A1 | 2/2013 | Penninger et al. |
| 2013/0185310 | A1 | 7/2013 | De Guise et al. |
| 2015/0208981 | A1 | 7/2015 | Oh et al. |
| 2016/0283681 | A1 | 9/2016 | Falck et al. |
| 2017/0228557 | A1* | 8/2017 | Kaditz ................ G06F 21/6218 |
| 2018/0101645 | A1* | 4/2018 | Sorenson ......... G06V 30/19167 |

OTHER PUBLICATIONS

International Search and Written Report Opinion for International Application No. PCT/EP2019/069302, filed Jul. 17, 2019, 26 pages.
Dimitrov, et al., "Analyzing Sounds of Home Environment for Device Recognition", In: Distributed Computing: 19th International Conference DISC 2005, Cracow, Poland, Sep. 26-29, 2005, Dec. 12, 2014, vol. 8850, pp. 1-16.
Rong, F., "Audio classification method based on machine learning", 2016 International Conference on Intelligent Transportation, Big Data & Smart City, IEEE, Dec. 17, 2016, pp. 81-84.

* cited by examiner

CROSS-VENDOR CROSS-MODALITY IMAGING WORKFLOW ANALYSIS

RELATED APPLICATIONS

This application is the U.S. National Phase application under 35 U.S.C. § 371 of International Application No. PCT/EP2019/069302, filed on Jul. 17, 2019, which claims the benefit and priority to Provisional Application No. 62/702,462, filed Jul. 24, 2018, which is incorporated by referenced in its entirety.

FIELD

The following relates generally to medical imaging procedure optimization and imaging data security.

BACKGROUND

Detailed workflow analysis in radiology is of increasing importance. Workflow analysis can enable workflow and scan protocol optimization, quality assurance for radiological procedures, automated real-time scheduling, or other automated assistance to operating staff. Conventional cross-vendor radiology process analysis is restricted to using data from a hospital network, such as HL7 and DICOM. However, these data sources do not contain any detailed information about the workflow on the imaging systems.

When considering data sources for detailed imaging workflow analysis of imaging devices in a hospital or the like, the modality log file includes all information about operation of the system. This information can be used for magnetic resonance (MR) and computed tomography (CT) to analyze machine utilization, identify repeated or aborted scans, unusual delays, and identify non-optimal sequence parameters. While information from the hospital network is usually available to analyze the workflow of the whole radiology department, the valuable internal information from the imaging equipment (e.g., from modality log files) is only available to the respective machine vendors. Since hospitals and radiology departments often use imaging devices from multiple vendors (i.e., manufacturers), one vendor is typically unable to use log file information from other vendors' imaging equipment, which inhibits the development of vendor-independent workflow analysis platforms that can observe the radiology workflow at a high level of detail. A particular problem is that vendor-specific operational data can potentially involve data privacy or trade secret issues, and therefore the modality log file is not shareable or useable for cross-vendor solutions.

The following discloses certain improvements.

SUMMARY

In one disclosed aspect, a system that facilitates determining usage patterns of medical imaging equipment across a plurality of vendors by recognizing patterns in sensor data comprises one or more sensors installed in a data security zone, in which an imaging device is installed. The system further comprises a preprocessing unit configured to: receive from the one or more sensors raw data associated with an imaging procedure being performed in the data security zone; extract one or more features from the raw data; generate a feature pattern that omits patient information and vendor-specific imaging device information; and transmit the feature pattern to a processing unit outside the data security zone. The processing unit is further configured to perform pattern analysis and identify the imaging procedure represented by the feature pattern by executing a machine learning algorithm that compares the received feature pattern to reference feature patterns for one or more imaging workflows.

In another disclosed aspect, a method for preprocessing data received from sensors that monitor medical imaging equipment within a data security zone comprises receiving input data from one or more sensors installed in the data security zone, extracting one or more features from the received input data, and generating a reduced data set comprising an extracted feature pattern describing an imaging procedure occurring within the data security zone for transmission out of the data security zone, wherein the reduced data set omits patient information and vendor-specific imaging device information. The method further comprises transmitting the extracted feature pattern out of the data security zone for analysis.

In another disclosed aspect, a method for processing an extracted feature pattern describing a medical imaging procedure and received from within a data security zone comprises receiving the extracted feature pattern from within the data security zone, and performing pattern analysis on the received feature pattern by comparing the received feature pattern to one or more known reference patterns. The method further comprises identifying the imaging procedure type and imaging parameters represented by the received feature pattern, and determining imaging procedure progress based on a comparison of the received feature pattern to known reference patterns for scans of the same type and having the same parameters.

One advantage resides in improving radiological workflow analysis, independent of imaging system vendors.

Another advantage resides in optimizing radiological workflow.

Another advantage resides in improving quality assurance in radiology.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

The herein-described systems and methods overcome these problems by acquiring the necessary detailed information about the usage patterns of imaging equipment in a cross-vendor approach by pattern recognition of sensor data, without modifying the system hardware or software. The described systems and methods also protect data privacy: sensor data is pre-processed on an isolated processing unit to remove any sensitive information and keep a selection of features only. Neither the vendors (manufacturers) nor the customers (hospitals, radiology departments, etc.) are able to access the raw sensor data that may potentially contain sensitive information.

To this end, the described systems and methods comprise several features that facilitate protecting sensitive vendor information while permitting use of the information contained in an imaging device's modality log file. A set of dedicated external sensors that can be installed at existing imaging equipment is provided to collect raw data regarding an imaging procedure, and a feature extraction algorithm is implemented on an isolated processing unit within a data security zone to convert the sensor signals to "fingerprints" (extracted feature patterns) of imaging procedures and to remove any sensitive information (e.g., vendor-specific information, patient identity information, etc.). A user interface is provided to train a machine learning algorithm by entering labelling information to match the acquired feature data. A pattern analysis algorithm compares acquired "fingerprints" with known patterns, producing output information about the identified acquisition protocol or procedure step. Additionally, a method is provided to correlate the procedure information to scheduling information from the hospital network (RIS) and thereby estimate the status of the ongoing examination.

Figure 1:
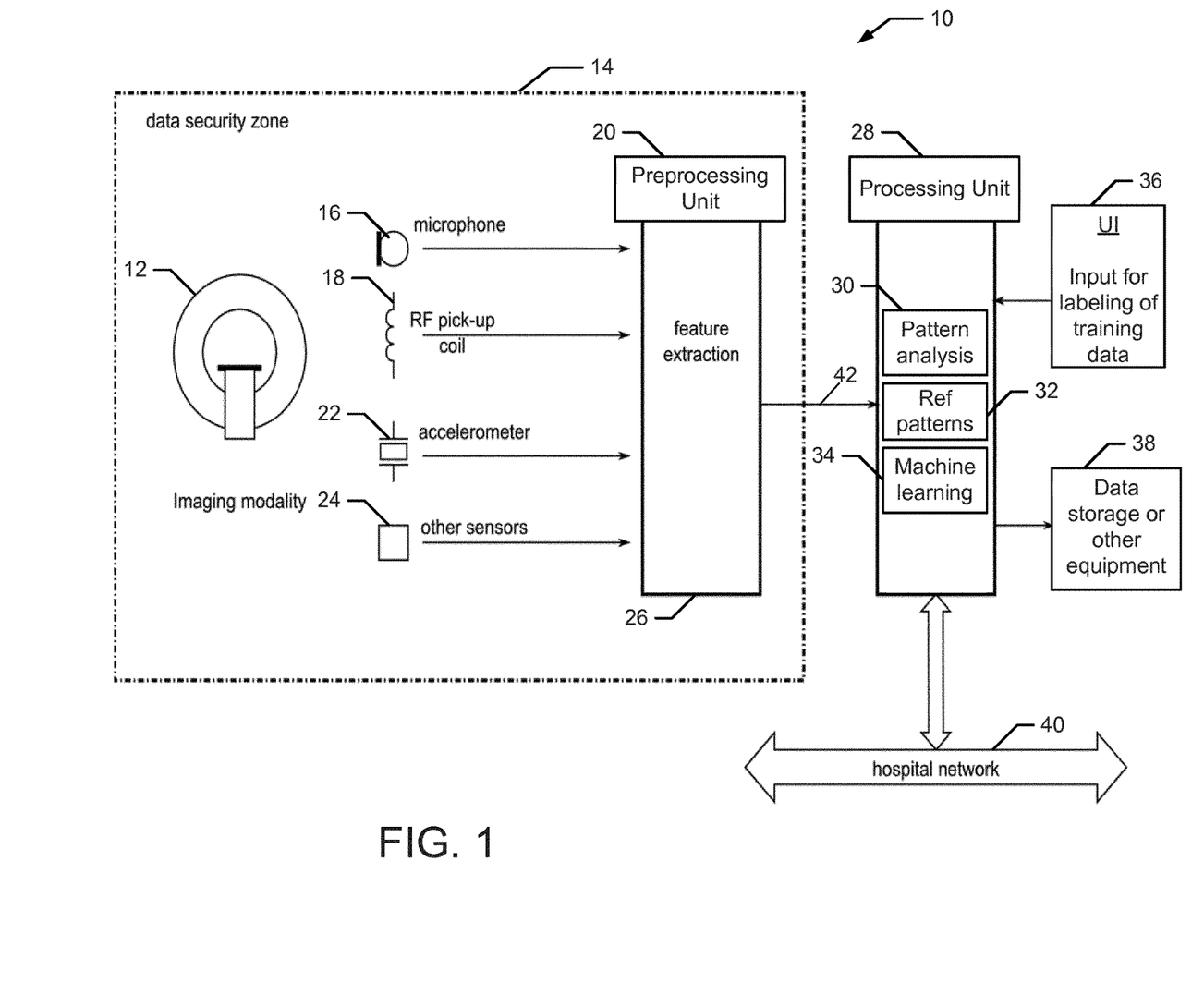
FIG. 1 illustrates a block diagram showing a system wherein different imaging modalities can be connected and a selection of sensors is to be adapted to the selected imaging modality.

FIG. 1 illustrates a block diagram showing a system 10 wherein different imaging modalities can be connected and a selection of sensors is to be adapted to the selected imaging modality 12. The system includes a data security zone 14, within which the actual sensor-based collection of data takes place and potentially sensitive data, such as conversations recorded by a microphone 16 or vendor-dependent radio frequency (RF) coil 18 signals may be present. A pre-processing unit 20 converts the raw data from the selected sensors to features that cannot be traced back to any sensitive information (i.e., vendor-specific information that may disclose trade secrets, sensitive procedural or functional information, etc.). Only the desensitized information leaves the data security zone. The system is designed in such a way that no sensitive information can leave the data zone and such that vendors are not permitted to access the raw sensitive data of a competitor.

Regarding the sensors, one or several sensors are installed near the imaging machine. For instance, a microphone 16 can be installed to measure acoustic signals (e.g., sequence timing for MR, gantry rotation frequency for CT, etc.). An RF pick-up coil 18 can be installed and tuned to the Larmor frequency for a specific MR field strength, to measure RF pulse timing and relative intensities (e.g., for MR, etc.), or the like. An accelerometer 22 can be installed and attached to the patient table on the imaging device to measure table motion (e.g., for MR, CT, interventional X-ray (iXR), etc.). In another embodiment, an accelerometer 22 is attached to a C-arm on the imaging device 12 to detect imaging system motion and angulation (e.g., for iXR, digital X-ray (DXR), etc.).

Other sensors 24 that may be employed within the data security zone include current probes around gradient coil supply cables (e.g., for MR, etc.), current probes around RF amplifier power cables (e.g., for MR, etc.), current probes around CT power cables (e.g., for CT). Additionally or alternatively, an X-ray detector can be installed for measuring scattered radiation for dose estimation and estimation of tube voltage (e.g., for CT, x-ray, etc.).

When the imaging modality is ultrasound (US), an ultrasound receiver can be installed near the patient or on an ultrasound head to collect raw data. Additionally, acceleration and gyroscopic sensors can be attached to the ultrasound head to estimate angulation and movement.

In the case of MR, sensors installed close to the scanner can be connected using throughputs in the MRI system's RF shielding. In one implementation, only a microphone need be used, which be installed outside the RF-shield, for example attached to the RF door from the outside. If no real-time, but rather only retrospective analysis is required, an alternative embodiment involves equipping the sensors with data loggers and internal storage, wherein data is collected at certain intervals by connecting a read-out unit to the sensor and copying the collected data. In another embodiment, a camera and image analysis software are installed to detect hardware used, such as MR coils used in certain exams.

The system 10 also comprises the preprocessing unit 20 within the data security zone 14. The pre-processing unit executes a feature extraction module 26 to extract features from the signals measured by the respective sensors. These features later serve as a "fingerprint", i.e. a pattern to uniquely identify a scan protocol. The pre-processing unit does not store the raw data collected by the sensors, nor is it connected to a network directly. In this way, it can be assured that sensitive raw data picked up by the sensors cannot be accessed. Sensitive data may comprise, for example, human voices and communication, or the exact shape of the RF pulse implemented in a competitor's system.

The interface between the pre-processing unit and the processing unit only allows a reduced dataset, i.e., the features, to be transferred. The features are designed to exclude sensitive data, in the sense of patient data or competitor's trade secrets. The extracted features permitted to leave the data security zone have a lower information content, and much lower dimensionality, than the raw data. For example, acoustic features specifying only mean amplitudes of a few frequency bands cannot be used to recover the contents of human speech (i.e., the conversation represented by the acoustic features), and thus acoustic features permitted to leave the data security zone cannot be used by a competitor to reconstruct information about the vendor's product. Similarly, a limitation of the measured data to only the main frequencies or phases, or an aggregation to mean values, ensures that no trade secrets about the exact implementation of the protocols are transmitted out of the data security zone. However, the foregoing information is sufficient for a determination by the processing unit as to the identity of the type of scan being performed in the data security zone, as well as other parameters associated therewith.

Examples of features that can be transmitted out of the data security zone include, without being limited to: timestamps of start and end of a scan, determined by start and end points of a continuous audio signal or RF pattern; acoustic frequency spectrum or selected single frequency amplitudes for MR or CT, restricted to a minimum amplitude level and frequency band, so that only imaging-related information is included and voices cannot be identified; relative RF amplitudes of RF pulse trains (e.g., for MR); relative phase of RF amplitude and acoustic signal for the main common frequency component (e.g., for MR); and/or duration and direction of a table motion, measured by accelerometer.

Other examples of features that can be transmitted out of the data security zone include, without being limited to: main frequency components found in the current supply of gradient coil or RF amplifier (e.g., for MR); duration and rotation speed of CT gantry rotation; X-ray dose and tube voltage detected (e.g., for CT, x-ray, iXR); and/or the size of ultrasound imaging volume and motion patterns determined from acceleration sensors. All features can be modified by a fixed random mathematical transformation preserving the dimensionality of the feature space, inherent to the specific pre-processing unit and unknown from the outside. In this way it can be assured that features are usable for machine learning but do not correspond directly to any measured property.

Extracted features are transmitted out of the data security zone 14 by the preprocessing unit 20 to a processing unit 28. The processing unit 28 receives the features from the pre-processing unit 20, and executes a pattern analysis module 30 that compares the feature pattern with a set of known reference patterns 32, to identify the sequence type and sequence parameters. This is done using a machine learning algorithm 34, such as a support vector machine, decision tree, or neural network.

The machine learning algorithm is first trained with known reference patterns 32. These training data can be, for instance: calculated from prior knowledge or assumptions, e.g., typical temporal patterns to be expected for a certain MR image contrast; and/or learned from sequences running on the imaging system by manually labelling measured patterns with the corresponding procedure parameters and using a machine learning algorithm. In any case, a set of parameters is provided as labels to the training data sets, so that the machine learning algorithm can later calculate predictions for these parameters. Suitable labels may include, without being limited to: start and end time of an examination; start and end time of an individual scan within the examination; hardware used during the scan, e.g. coils; type of MR image contrast (e.g., T1w, T2w, DWI, . . . ); MR sequence timing parameters (e.g., TR, TE, . . . ); image resolution; number of MR image slices; MR slice orientation; and/or patient table motion. Other examples of suitable labels include: probability for each scan to be a repeated scan; X-ray dose and tube voltage for CT or x-ray examinations; approximate field of view along the patient axis; pitch for CT examinations; frequency, acquisition mode and approximate field of view for ultrasound (US) examinations; angulation and number of acquisitions for iXR/DXR; etc. In one embodiment, the labels are provided manually, e.g., via a user interface 36 connected to the processing unit to allow for input of the labels for each training data set acquired. Information generated by the processing unit 28 (e.g., trained machine learning algorithms, predicted workflows, etc.) is stored to a database 38 and/or transmitted to other equipment for use thereby.

In one embodiment, the processing unit 28 is further connected to the hospital network 40, to derive additional information about the ongoing examination. In this way, the clinical question or other information about the procedure can be acquired. This information can be used to improve the procedure identification by using prior knowledge about the most probable procedures to be run for the given clinical question, to estimate the state of the examination and the remaining examination time by comparing the identified procedures already run with a known typical workflow for the given clinical question, and/or to determine the start and end of the complete examination of one patient.

By comparing the estimated procedure information with prior knowledge (i.e., reference patterns for similar examinations), additional information can be derived by the processing unit 26, such as the probability that an MR scan, or a scan performed on any other modality equipped with sensors as described herein, has been stopped before being finished. The hospital network data thus can be included in the training label set for the machine learning algorithm. Furthermore, scan repetitions can be detected by comparing feature patterns of different scans within one examination.

Once the data has been processed by the processing unit 28, there are several applications to which the data can be useful. For instance, the parameters predicted by the machine learning algorithm correspond to the information that can be extracted from modality log files. It is thus possible to reconstruct imaging workflow timelines in the same fashion employed for log file data, even if access to these the log files is not available. The information can be used to construct generic workflow descriptions independent of the data source and the equipment vendor and to analyze the workflow of the whole radiology department.

In one embodiment, the pre-processing unit and processing unit are integrated into one piece of hardware. To avoid leakage of raw data (and to demonstrate that such a leakage is impossible), a data bus 42 between pre-processing unit and processing unit allows only low-bandwidth transmission and is easily observable, e.g. using an RS232 or RS485 transmission protocol or the like. In another embodiment, a digital optical coupler is used to prevent high-frequency modulations to be passed through the conductors unnoticed. In one embodiment, the bandwidth is restricted to a level sufficient to transmit the feature set ("fingerprint") for each imaging sequence (e.g., 1200 baud, 9600 baud, 19200 baud, or the like). By restricting the bandwidth available for transmission across the security zone border, transfer of large amounts of raw data is also restricted, which further ensures that sensitive data is not transmitted out of the security zone. The pre-processing unit can be further isolated by using batteries as power supply.

Figure 2:
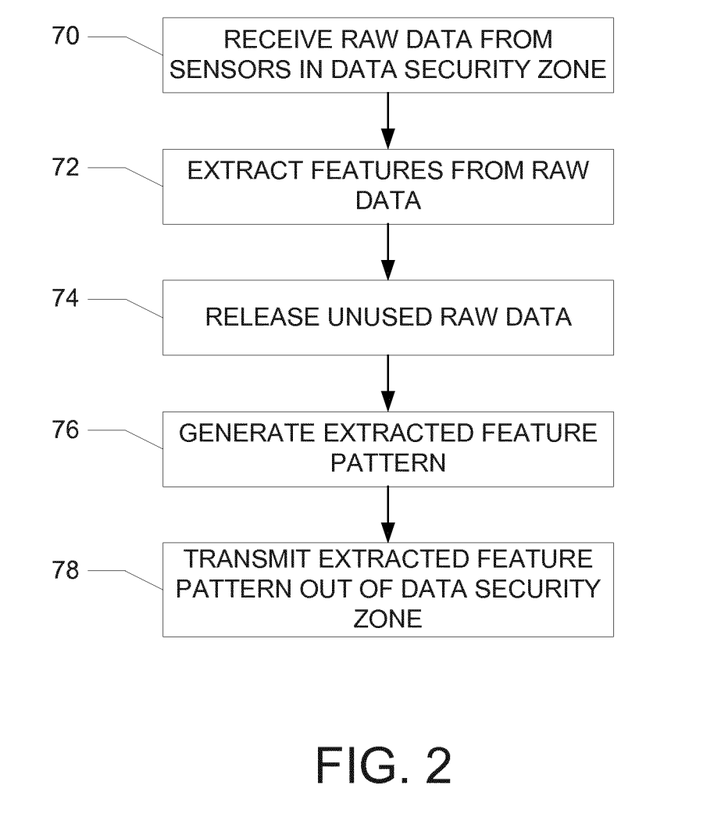
FIG. 2 illustrates a method for preprocessing data received from sensors within a data security zone to extract a scan fingerprint comprising a pattern of features derived from the sensor input, in accordance with various aspects described herein.

FIG. 2 illustrates a method for preprocessing data received from sensors within a data security zone to extract a scan fingerprint comprising a pattern of features derived from the sensor input, in accordance with various aspects described herein. At 70, input data is received from one or more sensors installed in the data security zone (e.g., in a room in which resides an imaging device and/or on the imaging device itself). Sensors may include, e.g., a microphone for measuring acoustic signals, RF pickup coils for measuring RF pulse timing and relative intensities, an accelerometer for measuring patient table motion and/or for detecting imaging system motion and angulation, current probes, an X-ray detector for measuring scattered radiation for dose estimation and estimation of tube voltage, an ultrasound detector, etc.

At 72, feature extraction is performed on the received sensor input to extract features from the signals measured by the respective sensors. These features later serve as a "fingerprint", i.e. a pattern to uniquely identify a scan protocol. At 74, raw data from which features are extracted is deleted or otherwise released, and is not stored. In this way, it can be assured that sensitive raw data picked up by the sensors cannot be accessed by a vendor's competitors or any unauthorized party. Sensitive raw data may comprise, for example, human voices and communication, or the exact shape of the RF pulse implemented in a competitor's system.

At 76, a reduced data set comprising the extracted feature pattern is prepared for transmission out of the data security zone. The features comprised by the feature pattern exclude sensitive data, including patient data and any information descriptive of the vendor's (the manufacturer of the imaging device(s) trade secrets. The extracted features permitted to leave the data security zone have a lower information content and dimensionality than the raw data. For example, if the raw data comprises a human conversation, the extracted acoustic features only describe mean amplitudes of a few frequency bands, and thus cannot be used to recover the contents the conversation. Thus, acoustic features permitted to leave the data security zone cannot be used by a competitor to reconstruct information about the vendor's product. Similarly, a limitation of the measured data to only main frequencies or phases, or an aggregation of mean values, ensures that no trade secrets about the exact implementation of the vendor's protocols are transmitted out of the data security zone.

Examples of features that can be transmitted out of the data security zone include, without being limited to: timestamps of start and end of a scan, determined by start and end points of a continuous audio signal or RF pattern; acoustic frequency spectrum or selected single frequency amplitudes for MR or CT, restricted to a minimum amplitude level and frequency band, so that only imaging-related information is included and voices cannot be identified; relative RF amplitudes of RF pulse trains (e.g., for MR); relative phase of RF amplitude and acoustic signal for the main common frequency component (e.g., for MR); and/or duration and direction of a table motion, measured by accelerometer.

Other examples of features that can be transmitted out of the data security zone include, without being limited to: main frequency components found in the current supply of gradient coil or RF amplifier (e.g., for MR); duration and rotation speed of CT gantry rotation; X-ray dose and tube voltage detected (e.g., for CT, x-ray, iXR); and/or the size of ultrasound imaging volume and motion patterns determined from acceleration sensors. Additionally, features can be modified by a fixed random mathematical transformation preserving the dimensionality of the feature space, inherent to the specific pre-processing unit and unknown from the outside. In this way it can be assured that features are usable for machine learning but do not correspond directly to any measured property (raw data).

At 78, the extracted feature pattern is transmitted out of the data security zone to a processing unit for analysis.

Figure 3:
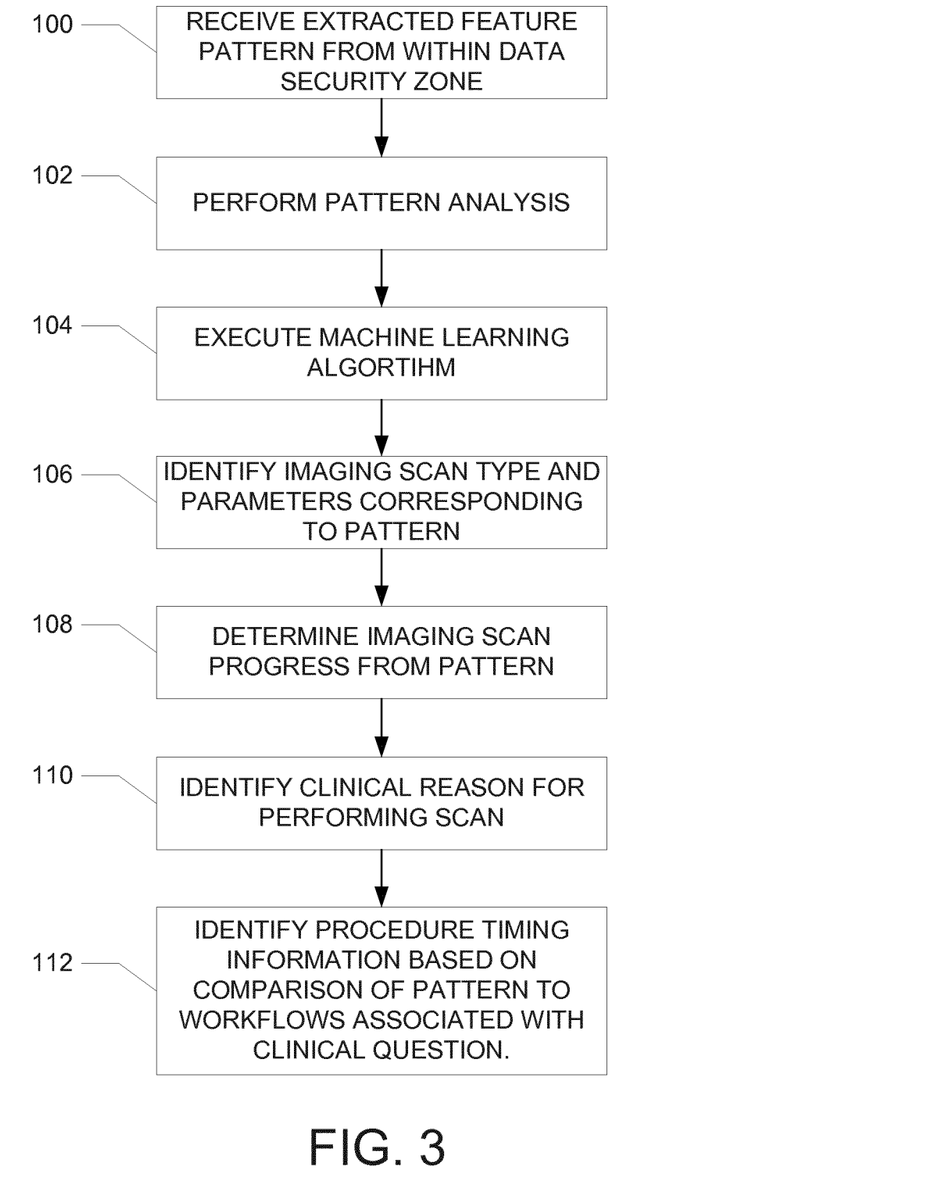
FIG. 3 illustrates a method for analyzing extracted feature patterns received from within a data security zone, in accordance with various aspects described herein.

FIG. 3 illustrates a method for analyzing extracted feature patterns received from within a data security zone, in accordance with various aspects described herein. At 100, one or more extracted feature patterns are received from within the data security zone. At 102, pattern analysis is performed to by comparing the received feature pattern with a set of known reference patterns. At 104, a machine learning algorithm is employed to identify the sequence type and sequence parameters (e.g., scan types, parameters employed during the scan such as frequency, duration, etc.) represented by the feature pattern. This is done using a machine learning algorithm, such as a support vector machine, decision tree, or neural network.

The machine learning algorithm employed at 104 is first trained with known reference patterns. These training data can be, for instance: calculated from prior knowledge or assumptions, e.g., typical temporal patterns to be expected for a certain MR image contrast or CT scan (or other imaging modality); and/or learned from sequences running on the imaging system by manually labeling measured patterns with the corresponding procedure parameters and using a machine learning algorithm. In any case, a set of parameters is provided as labels to the training data sets, so that the machine learning algorithm can later calculate predictions for these parameters. Suitable labels may include, without being limited to: start and end time of an examination; start and end time of an individual scan within the examination; hardware used during the scan, e.g. coils; type of MR image contrast (e.g., T1w, T2w, DWI, . . . ); MR sequence timing parameters (e.g., TR, TE, . . . ); image resolution; number of MR image slices; MR slice orientation; and/or patient table motion. Other examples of suitable labels include: probability for each scan to be a repeated scan; X-ray dose and tube voltage for CT or x-ray examinations; approximate field of view along the patient axis; pitch for CT examinations; frequency, acquisition mode and approximate field of view for ultrasound (US) examinations; angulation and number of acquisitions for iXR/DXR; etc. In one embodiment, the labels are provided manually, e.g., via a user interface connected to the processing unit to allow for input of the labels for each training data set acquired. Information generated by the processing unit (e.g., trained machine learning algorithms, predicted workflows, etc.) is stored to a database and/or transmitted to other equipment for use thereby.

Once the machine learning algorithm has been applied to the received feature pattern, the pattern is identified as corresponding to a particular scan type having particular scan parameters, at 106. At 108, scan progress is determined based on a comparison of the received feature pattern to known patterns for scans of the same type and having the same parameters. In one embodiment, the identified feature pattern is used to construct new generic workflows for similar scan types having similar scan parameters, but independent of the scan data source and equipment vendor information, and the updated workflows can be stored to a database for future algorithm training and/or feature pattern identification.

Additionally, information can be received from a hospital network during pattern analysis to derive additional information about an ongoing examination, in order to decipher the clinical question that prompted the scan or other information about the procedure, at 110. This information can be used to improve the procedure identification by using prior knowledge about the most probable procedures to be run for a given clinical question, to estimate the state of the examination and/or the remaining examination time by comparing the identified procedures already run with a known typical workflow for the given clinical question, and/or to determine the start and end of the complete examination of one patient. At 112, procedure timing information is determined based on a comparison of the received feature pattern information to one or more workflows associated with the identified clinical question.

By comparing the estimated procedure information with prior knowledge (i.e., reference patterns for similar examinations), additional information can be derived, such as the probability that an MR scan, or a scan performed on any other modality equipped with sensors as described herein, has been stopped before being finished. The hospital network data thus can be included in the training label set for the machine learning algorithm. Furthermore, scan repetitions can be detected by comparing feature patterns of different scans within one examination.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A system that facilitates determining usage patterns of medical imaging equipment across a plurality of vendors by recognizing patterns in sensor data, comprising:
one or more sensors installed in a data security zone in which an imaging device is installed, the one or more sensors comprising a radio frequency (RF) pickup coil that measures radio frequency in the data security zone, and wherein the data security zone is a zone in which sensitive data including vendor-dependent radio frequency coil signals can be measured from the radio frequency pickup coil;
a preprocessing unit configured to:
receive from the one or more sensors raw data associated with an imaging procedure being performed in the data security zone;
extract one or more features from the raw data, wherein the one or more features comprises one or more of: timestamps marking a start and an end of a scan, the timestamps determined by start and end points of an RF pattern; relative RF amplitudes of RF pulse trains; or a relative RF phase;
generate a feature pattern that omits patient information and vendor-specific imaging device information; and
transmit the feature pattern to a processing unit outside the data security zone;
wherein the processing unit is further configured to:
perform pattern analysis and identify the imaging procedure represented by the feature pattern by executing a trained machine learning algorithm that compares the received feature pattern to reference feature patterns for one or more imaging workflows.

2. The system according to claim 1, wherein:
the one or more sensors further comprise a microphone that captures acoustic signals in the data security zone, and wherein the timestamps marking a start and an end of a scan are determined by start and end points of a continuous audio signal; and
the one or more features further comprises at least one of an acoustic frequency spectrum and a selected single frequency amplitude that is restricted to a minimum amplitude level and frequency band, such that only imaging-related information is included and voices cannot be identified.

3. The system according to claim 1, wherein the RF pickup coil is tuned to a Larmor frequency for a specific magnetic resonance (MR) field strength in order to measure RF pulse timing and relative intensities.

4. The system according to claim 1, wherein the one or more sensors further comprises one or more accelerometers, and wherein at least one of:
an accelerometer is coupled to a patient table on the imaging device and configured to measure table motion; and
an accelerometer is coupled to a C-arm on the imaging device and configured to detect imaging system motion and angulation.

5. The system according to claim 1, wherein the imaging device comprises a magnetic resonance (MR) imaging device, and wherein the one or more sensors further comprises one or more current probes positioned at least one of:
around gradient coil supply cables for the MR imaging device;
around RF amplifier power cables for the MR imaging device.

6. The system according to claim 1, wherein the imaging device comprises a computed tomography (CT) imaging device, and wherein the one or more sensors further comprises at least one of:
one or more current probes positioned around power cables for the CT imaging device; and
an X-ray detector configured to measure scattered radiation for dose estimation and estimation of tube voltage.

7. The system according to claim 1, wherein the imaging device comprises an ultrasound (US) imaging device, and wherein the one or more sensors further comprises at least one of:
an ultrasound receiver positioned at least one of near the patient and on an ultrasound head to collect raw data; and
at least one of acceleration and gyroscopic sensors attached to the ultrasound head to estimate angulation and movement.

8. The system according to claim 1, wherein the machine learning algorithm comprises at least one of a support vector machine, decision tree, or neural network.

9. The system according to claim 1, wherein the processing unit is further configured to execute a pattern analysis module configured to compare the received feature pattern with the reference patterns, and to identify a sequence type and sequence parameters being used in the imaging procedure.

10. The system according to claim 1, wherein the processing unit is further configured to, when performing the feature pattern analysis, estimate procedure information comprising at least one of:
a state of the examination and remaining examination time; and
a start time and end time of a complete examination of a patient;
and wherein the processing unit is further configured to comparing the estimated procedure information to reference patterns for similar examinations, and to determine whether the scan has been stopped before being finished.

11. The system according to claim 1, wherein the processing unit is further configured to reconstruct one or more imaging workflow timelines without access to the log file data, and based on the one or more reconstructed imaging workflow timelines, construct generic workflow descriptions independent of data source and equipment vendor.

12. A method for processing an extracted feature pattern describing a medical imaging procedure and received from within a data security zone, comprising:
receiving input data from one or more sensors installed in the data security zone, the input data comprising radio frequency (RF) signal measurement information from a RF pickup coil in the data security zone, and wherein the data security zone is a zone within which sensitive data including vendor-dependent radio frequency coil signals can be measured from the radio frequency pickup coil;
extracting one or more features from the received input data, wherein the one or more features comprise one or more of: timestamps marking a start and an end of a scan, determined by start and end points of an RF pattern; relative RF amplitudes of RF pulse trains; or relative RF phase;

generating a reduced data set comprising an extracted feature pattern describing an imaging procedure occurring within the data security zone for transmission out of the data security zone, wherein the reduced data set omits patient information and vendor-specific imaging device information; and transmitting the extracted feature pattern out of the data security zone for analysis;

receiving the extracted feature pattern from within the data security zone;

performing pattern analysis on the received feature pattern and identifying the imaging procedure represented by the received feature pattern by comparing the received feature pattern to reference feature patterns for one or more imaging workflows comprising executing a trained machine learning algorithm.

13. The method according to claim 12, wherein:

the input data further comprises acoustic signals from at least one microphone in the data security zone, and wherein the timestamps marking a start and an end of a scan are determined by start and endpoints of a continuous audio signal; and the one or more features further comprise at least one of an acoustic frequency spectrum and a selected single frequency amplitude that is restricted to a minimum amplitude level and frequency band, such that only imaging-related information is included and voices cannot be identified.

14. The method according to claim 12, wherein the RF pickup coil is tuned to a Larmor frequency for a specific magnetic resonance (MR) field strength in order to measure RF pulse timing and relative intensities.

15. The method according to claim 12, wherein receiving input data comprises receiving motion information from one or more accelerometers, and wherein at least one of:

an accelerometer is coupled to a patient table on the imaging device and configured to measure table motion; and an accelerometer is coupled to a C-arm on the imaging device and configured to detect imaging system motion and angulation.

16. The method according to claim 12, wherein the imaging procedure comprises a magnetic resonance (MR) imaging procedure, and wherein receiving input data comprises receiving data from one or more current probes positioned at least one of:

around gradient coil supply cables for an MR imaging device;

around RF amplifier power cables for an MR imaging device.

17. The method according to claim 12, wherein the imaging procedure comprises a computed tomography (CT) imaging procedure, and wherein receiving input data comprises receiving data from at least one of:

one or more current probes positioned around power cables for the CT imaging device; and an X-ray detector configured to measure scattered radiation for dose estimation and estimation of tube voltage.

18. The method according to claim 12, comprising:

identifying the imaging procedure type and imaging parameters represented by the received feature pattern; and determining imaging procedure progress based on a comparison of the received feature pattern to known reference patterns for scans of the same type and having the same parameters.

19. The method according to claim 18, further comprising:

receiving information from a hospital network during pattern analysis and identifying a clinical question that prompted the scan; and determining imaging procedure timing information based on a comparison of the received feature pattern information to one or more workflows associated with the identified clinical question.

20. The method according to claim 18, wherein the machine learning algorithm comprises at least one of a support vector machine, decision tree, or neural network.

* * * * *